(12) United States Patent
Vaccaro et al.

(10) Patent No.: US 9,238,125 B2
(45) Date of Patent: Jan. 19, 2016

(54) INFLATION DEVICE FOR BALLOON SINUS DILATION

(71) Applicant: Medtronic Xomed, Inc., Jacksonville, FL (US)

(72) Inventors: Robert K. Vaccaro, Ponte Vedra Beach, FL (US); Timothy M. Furst, Ponte Vedra, FL (US); Wenjeng Li, Saint Johns, FL (US); David J. Little, II, Ponte Vedra, FL (US); Ali Mowlai-Ashtiani, Jacksonville, FL (US); Dana A. Oliver, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 137 days.

(21) Appl. No.: 13/755,934

(22) Filed: Jan. 31, 2013

(65) Prior Publication Data
US 2014/0213968 A1 Jul. 31, 2014

(51) Int. Cl.
*A61M 29/00* (2006.01)
*A61M 25/10* (2013.01)
*A61M 29/02* (2006.01)

(52) U.S. Cl.
CPC ..... *A61M 25/1018* (2013.01); *A61M 25/10182* (2013.11); *A61M 25/10187* (2013.11); *A61M 29/02* (2013.01)

(58) Field of Classification Search
CPC ............ A61M 25/1018; A61M 29/02; A61M 25/10182; A61M 25/10187
USPC ...................... 604/96.01, 97.02–97.03, 99.01, 604/100.01–100.03
See application file for complete search history.

(56) References Cited

U.S. PATENT DOCUMENTS

| 5,213,115 | A | 5/1993 | Zytkovicz et al. |
| 5,449,344 | A | 9/1995 | Taylor et al. |
| 6,110,144 | A * | 8/2000 | Choh et al. ................. 604/99.01 |
| 2006/0004323 | A1* | 1/2006 | Chang et al. .................... 604/28 |
| 2006/0009779 | A1 | 1/2006 | Collins et al. |
| 2010/0179488 | A1 | 7/2010 | Spiegel et al. |
| 2010/0211007 | A1 | 8/2010 | Lesch, Jr. et al. |
| 2010/1211007 | | 8/2010 | Lesch, Jr. et al. |
| 2011/0054395 | A1 | 3/2011 | O'Dea et al. |

FOREIGN PATENT DOCUMENTS

| EP | 2236168 | 10/2010 |
| WO | 9207609 | 5/1992 |

OTHER PUBLICATIONS

PCT Search Report and Written Opinion, PCT/US2014/012974, date of mailing May 21, 2014, 14 pages.

* cited by examiner

*Primary Examiner* — Rebecca E Eisenberg
(74) *Attorney, Agent, or Firm* — Dicke, Billig & Czaja, PLLC

(57) ABSTRACT

An inflation device useful for inflating a balloon provided with a surgical instrument, such as a balloon sinus dilation instrument. The inflation device includes a syringe, a connector, and mechanical pressure indicator. The syringe includes a plunger slidably disposed within a barrel. The connector is configured to fluidly connect an outlet of the syringe with a surgical instrument balloon in establishing a closed inflation system between the syringe and an interior of the balloon. The pressure indicator is associated with the syringe and is configured to transition from a non-alert state to an alert state when a pressure of the inflation system has reached a predetermined level. In some embodiments, the inflation device is characterized by the absence of a pressure gauge.

19 Claims, 11 Drawing Sheets

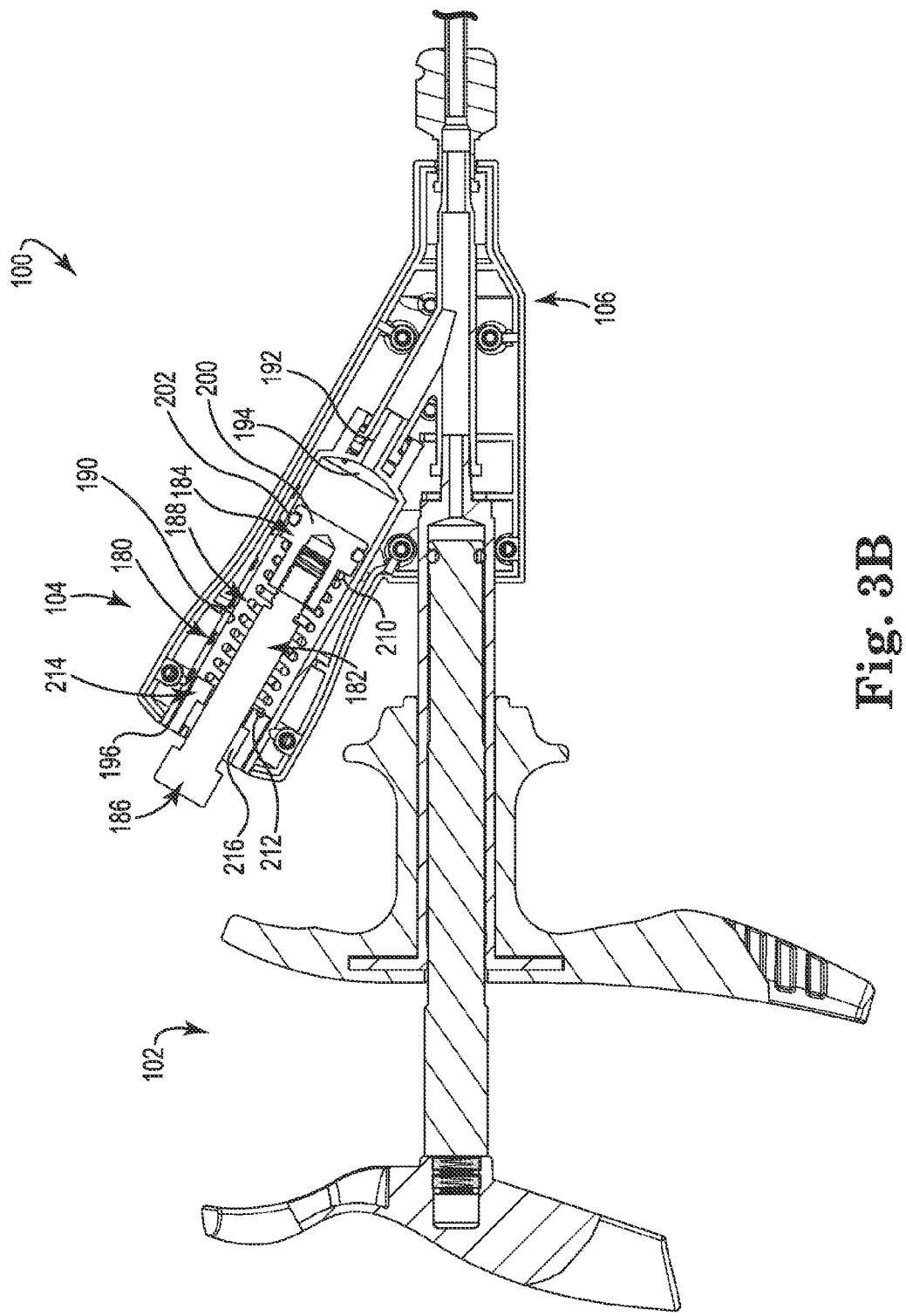

INFLATION DEVICE FOR BALLOON SINUS DILATION

BACKGROUND

The present disclosure relates to sinus dilation systems and methods. More particularly, relates to inflation devices useful with balloon-based surgical instruments, such as balloon sinus dilation instruments for dilating a portion of a patient's paranasal sinuses in the treatment of sinusitis and other disorders.

The paranasal sinus system is a grouping of four pairs of air-filled cavities that are named for the facial bones in which they are located. The maxillary sinuses surround the nasal cavity, the frontal sinuses are above the eyes, the ethmoid sinuses are between the eyes, and the sphenoid sinuses are within the sphenoid bone at the center of the skull base under the pituitary gland. The paranasal sinuses are lined with respiratory epithelium, are joined to the nasal cavity via small orifices called ostia, and contain secretory tissue that produces a large volume of mucus. This mucus is normally relieved from the sinuses in a specific pattern through the corresponding ostia.

The mucus membrane that lines the paranasal sinuses can become inflamed. This inflammation is known as sinusitis (or rhinosinusitis), and can be caused by various factors such as bacteria, viruses, allergies, anatomical abnormalities, etc. If the mucosa of one of the paranasal sinus passageways becomes inflamed, the passageway can become blocked, trapping mucus. Patients suffering from sinusitis can experience a number of symptoms or complications, such as headache, facial pain, toothache, inner ear problems, etc.

Sinusitis is typically classified as acute (infection lasting 4 or less weeks) or chronic. Many instances of acute sinusitis can be effectively treated with medication (e.g., antibiotics, antihistamines, etc.). Chronic sinusitis may implicate a more invasive treatment option in which the paranasal passageways or affected sinuses are surgically accessed. Conventional sinus surgery entails an incision formed along the side of the nose or through the gums of the upper teeth to provide access to the targeted sinus anatomy. Once accessed, the paranasal sinus passageway in question is surgically enlarged or otherwise altered to facilitate resumption of mucus clearance.

More recently, corrective sinus surgery has been performed endoscopically, minimizing external trauma to the patient. With functional endoscopic sinus surgery (FESS) an endoscope is inserted into the nose. Using visualization through the endoscope, the anatomical and pathological obstructions associated with the sinusitis are removed in order to restore normal mucus clearance. The benefit of FESS (and other intranasal procedures) is the ability to allow for a more targeted approach to the affected sinuses, reducing tissue disruption and minimizing post-operative complications.

An even more recent minimally invasive, intranasal sinus surgery is known as balloon sinus dilation or balloon sinuplasty. Balloon sinus dilation (or simply "sinus dilation") was initially developed to address the post-operative pain and bleeding associated with FESS. In general terms, conventional sinus dilation is an endoscopic, catheter-based procedure for treating sinusitis using a small, flexible balloon catheter to enlarge or dilate the affected sinus passageway(s). When the balloon is correctly located and inflated, it widens the walls of the sinus passageway, with the goal of restoring normal drainage without damaging the sinus lining.

When performing sinus dilation, the surgeon inserts a sinus guide catheter or cannula through the nostril (or naris) to gain access to the affected sinus ostia (opening) under endoscopic visualization. A guide wire and/or illumination system are then introduced into the targeted sinus via the sinus guide catheter. Once access to the intended targeted location is confirmed by light or fluoroscopy, a flexible catheter, carrying a balloon, is introduced into the sinus cavity over the sinus guide wire, locating the balloon in the blocked ostium. In this regard, the illumination system provides transcutaneous (through the skin) light transmission that the surgeon relies upon when estimating desired balloon placement. Once the desired balloon position has been visually confirmed, the balloon is gradually inflated to dilate the narrowed or blocked ostium. The balloon is then deflated and removed. Next, an irrigation catheter may be advanced over the guide wire to flush out mucus. Finally, the sinus irrigation catheter is removed from the sinus to allow the sinus cavity to drain any mucus.

While highly promising, existing sinus dilation systems and methods have several drawbacks. As highlighted by the above, available sinus dilation systems require multiple steps and multiple instruments. While the guide wire can facilitate accessing the targeted sinus site and use of a flexible balloon catheter, surgeons must be trained in the correct use of the guide wire, and the guide wire represents an added cost. Further, the required illumination source and use thereof is time-consuming and relatively expensive. Moreover, a surgeon is required to estimate a location of the targeted ostium only by illumination through the patient's skin. In some instances, the guide wire and/or illumination source may inadvertently be located in a "blind hole". As a point of reference, regions of the sinus system are pneumatized by various cells in most patients. These cells can build over time, collectively creating an anatomic variation. In some instances, for example, Type II cells can occur at the frontal sinus and can progress to a level that is grossly akin to the frontal sinus ostium. It is estimated that as many as 25% of patients suffering from sinusitis of the frontal sinus have Type II cells. When internally illuminated (and viewed externally), a region of the Type II cell cluster may appear (or "feel") quite similar to the natural frontal sinus ostium, leading the surgeon to incorrectly assume that the desired ostium has been accessed. When the balloon is subsequently inflated, it may actually occlude the ostium rather than open the ostium.

In addition to the above concerns, the inflation devices utilized with available sinus dilation systems have several drawbacks. As a point of reference, balloon catheters have long been employed for various surgical procedures (e.g., angioplasty, intravascular stent deployment, kyphoplasty, etc.), and inflation devices well-suited for these applications are widely available. Although the anatomical constraints and performance requirements associated with balloon sinus dilation are quite different from other balloon catheter procedures, existing balloon sinus dilation systems default to the already-available inflation devices. Available inflation devices are typically quite large (in order to maintain a sufficient volume of inflation fluid), full featured (e.g., include one or more gauges that display pressure(s) within the device), and complicated to use. For example, mechanical pressure gauges (with dial-type display), electronic pressure gauges (with digital-type display), are included with available balloon catheter inflation devices. While necessary for many balloon catheter procedures, a constant display of current system pressure is of less importance with balloon sinus dilation. These gauges render existing inflation devices highly expensive, especially where the inflation device is intended to be disposable. Further, the gauge(s) may need to be calibrated prior to each use, thereby increasing the time required to complete the procedure. Conversely, other, lesscomplex inflation devices (e.g., a simple syringe) provide no indication of system pressure, and are void of any warnings when system pressure exceeds a particular level.

In light of the above, a need exists for improved inflation devices useful with sinus dilation systems and other balloon-based surgical procedures.

SUMMARY

Aspects of the present disclosure relate to an inflation device useful for inflating a balloon provided with a surgical instrument, such as a balloon sinus dilation instrument. The inflation device includes a syringe, a connector, and mechanical pressure indicator. The syringe includes a plunger slidably disposed within a barrel. The connector is configured to fluidly connect an outlet of the syringe with a surgical instrument balloon in establishing a closed inflation system between the syringe and an interior of the balloon. The pressure indicator is associated with the syringe and is configured to transition from a non-alert state to an alert state when a pressure of the inflation system has reached a predetermined level. In some embodiments, the inflation device is characterized by the absence of a pressure gauge. In other embodiments, the pressure indicator includes a housing maintaining a spring and an indicator body. The spring biases the indicator body to the non-alert state in which the indicator body is visually obscured when exteriorly viewing the pressure indicator. When the inflation system pressure rises to a predetermined level, a biasing force of the spring is overcome, and the indicator body transitions to the alert state in which the indicator body can be visually perceived (and possibly tactilely perceived) when exteriorly viewing the pressure indicator.

Other aspects in accordance with principles of the present disclosure relate to an inflation device useful for inflating a balloon of a surgical instrument, the device including a syringe, a connector, and an over pressure controller. The syringe includes a plunger slidably disposed within a barrel. The connector is configured to fluidly connect an outlet of the syringe with a surgical instrument balloon in establishing a closed inflation system between the syringe and an interior of the balloon. The over pressure controller is associated with the syringe and is configured to regulate inflation system pressure (e.g., incrementally increase a volume of the inflation system) once a pressure of the inflation system has reached a predetermined level. In some embodiments, the over pressure controller is configured to provide, and can self-transition from, a normal state. When the inflation device is connected to surgical instrument balloon to create the closed inflation system, the over pressure controller is fluidly open to the inflation system and defines a portion (or "over pressure controller volume") of an overall available volume of the closed inflation system. In the normal state, the over pressure controller volume remains substantially constant. Once the inflation system pressure reaches the predetermined level, the over pressure controller self-transitions from the normal state, increasing the over pressure controller volume component of the overall inflation system volume and relieving or accumulating developed pressure. Where an attempt is made by a user to further increase a pressure of the inflation system beyond the predetermined pressure level via continued operation of the syringe, the over pressure controller effectuates control over the inflation system pressure, limiting the rate at which the inflation system pressure can be increased with incremental operation of the syringe. In some embodiments, the over pressure controller, alone or in combination with a construction of the syringe, is configured to prevent the inflation system pressure from exceeding a maximum level. In other words, the over pressure controller, in the normal state, permits inflation system pressure to increase incrementally with operation of the syringe up to the predetermined pressure level. Once the predetermined pressure level has been attained, the over pressure controller transitions from the normal state; with further operation of the syringe, the inflation system overall pressure can be increased beyond the predetermined pressure level, but at a rate that is less than a rate than would otherwise be achieved were the over pressure controller not provided. The over pressure controller may, or may not, be configured to provide a visual indication to a user when transitioning from the normal state.

BRIEF DESCRIPTION OF THE DRAWINGS

FIG. 3B is a cross-sectional side view of the portion of the inflation device, of FIG. 3A in an alert state;

DETAILED DESCRIPTION

Figure 1:
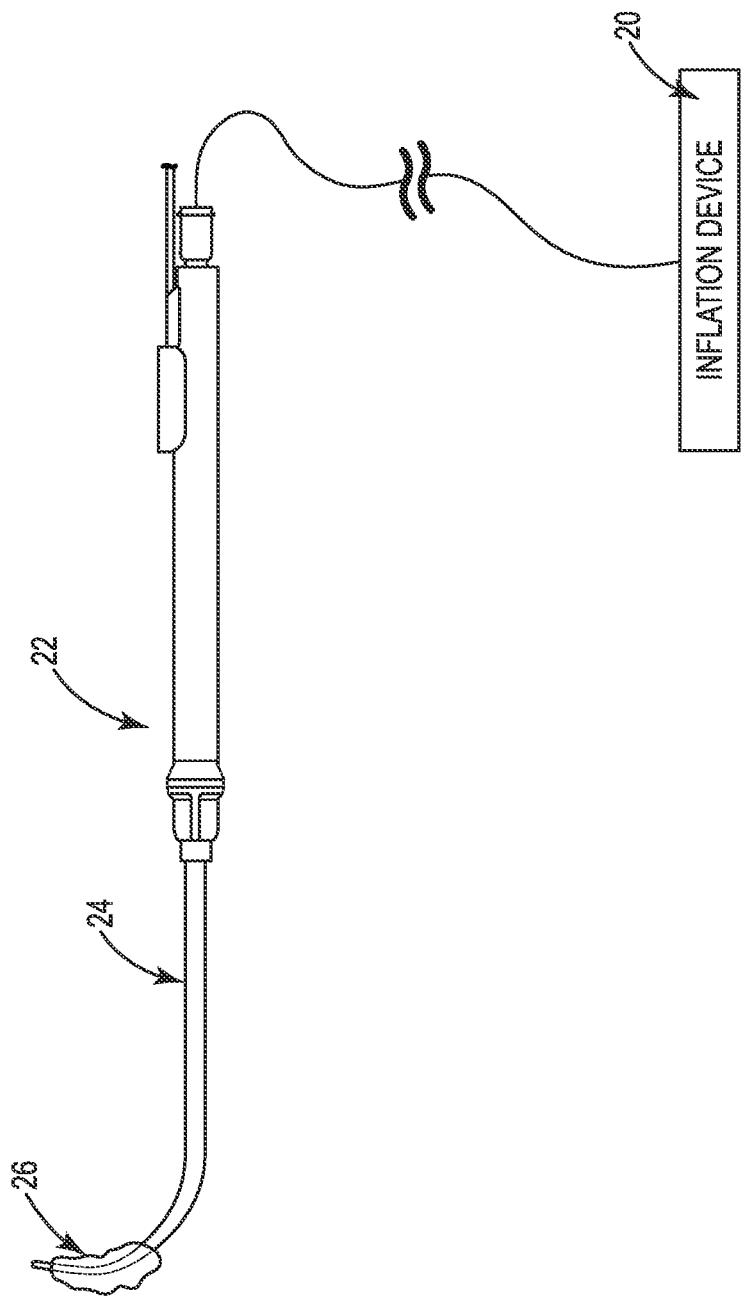
FIG. 1 is a schematic illustration of a surgical system including an inflation device and a balloon sinus dilation instrument.

Aspects of the present disclosure relate to inflation devices useful with balloon-based (or balloon-carrying) surgical instruments, for example, with sinuplasty and other balloon-based paranasal sinus procedures. The inflation devices of the present disclosure can be provided as a stand-alone device, or can be included as part of a surgical system some examples of which are described in U.S. application Ser. No. 13/725,716 entitled "Sinus Dilation System and Method" filed Dec. 21, 2012 and the disclosure of which is incorporated herein by reference in its entirety. In general terms, and as shown in FIG. 1, inflation devices 20 of the present disclosure can be used with a sinus dilation instrument 22. The sinus dilation instrument 22 can assume a wide variety of forms, and more generally includes a probe (e.g., a rod or tube) 24 carrying a balloon 26. The probe 24 is sized and shaped to deliver the balloon 26 to a paranasal sinus target site (e.g., a sinus ostium) via a patient's nostril or naris or other conventional approach such as canine fossa or open approach. Once positioned, the inflation device 20 is operated to inflate the balloon 26, with the so-inflated balloon dilating the target site. As described below, the inflation devices 20 of the present disclosure do not include any pressure gauges (mechanical or electrical) and do not display pressure readings. However, the inflation devices 20 will alert a user when a desired inflation pressure is reached. Thus, the simplified inflation devices 20 of the present disclosure are, as compared to conventional surgical balloon catheter inflation devices, highly cost effective and intuitive/easy to use.

Figure 2A:
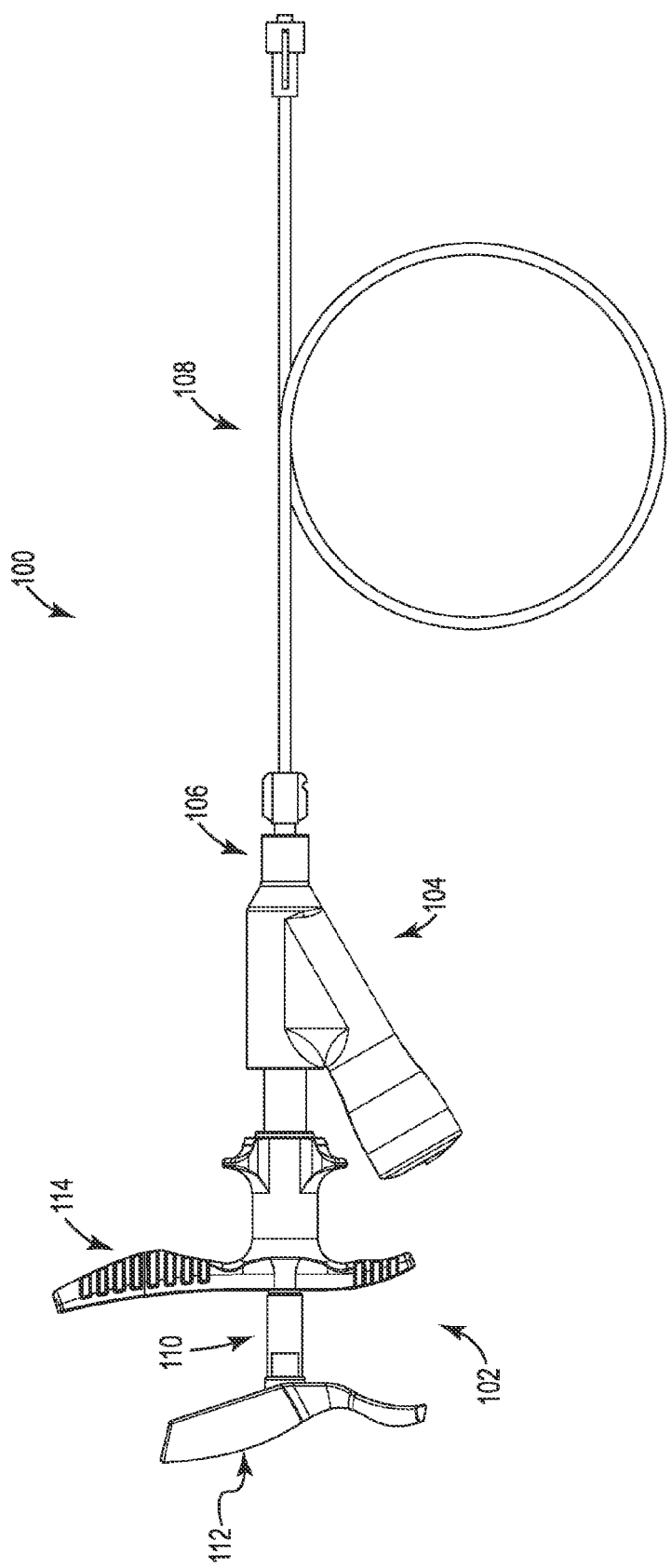
FIG. 2A is a side view of an inflation device in accordance with principles of the present disclosure and in a non-alert state.
Figure 2B:
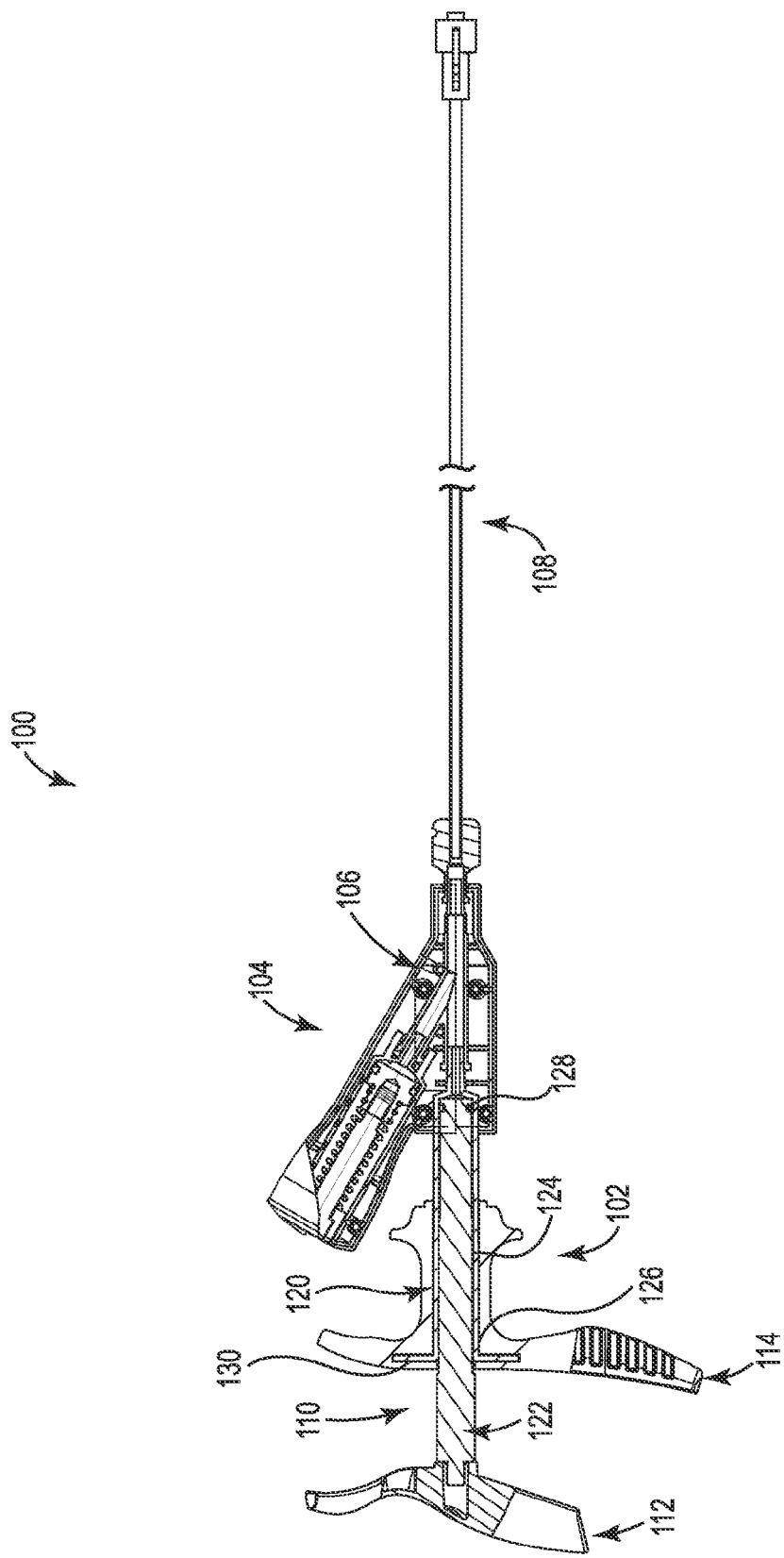
FIG. 2B is a cross-sectional view of the inflation device of FIG. 2A.

With the above in mind, one embodiment of an inflation device 100 in accordance with principles of the present disclosure and useful with sinus dilation instruments is shown in FIGS. 2A and 2B. The inflation device 100 includes a syringe assembly 102, a mechanical pressure indicator or over pressure controller 104, a connector assembly 106, and optional tubing 108. Details on the various components are provided below. In general terms, the syringe assembly 102 is manually operable to deliver pressurized fluid (e.g., for inflating the sinus dilation instrument balloons of the present disclosure). The mechanical pressure indicator 104 is fluidly connected to an outlet of the syringe assembly 102 via the connector assembly 106 and provides a visual indication (e.g., transitions from a normal or non-alert state of FIG. 2B (also shown in FIG. 3A) to an alert state (shown in FIG. 3B)) when a pressure of fluid at the syringe assembly 102 reaches a pre-determined level, and optionally limits operation of the syringe assembly 102 once the pre-determined level has been reached. The tubing 108, where provided, can be of a conventional form for fluidly connecting an outlet of the connector assembly 106 with the sinus dilation instrument 22 (or other instrument of interest).

Figure 3A:
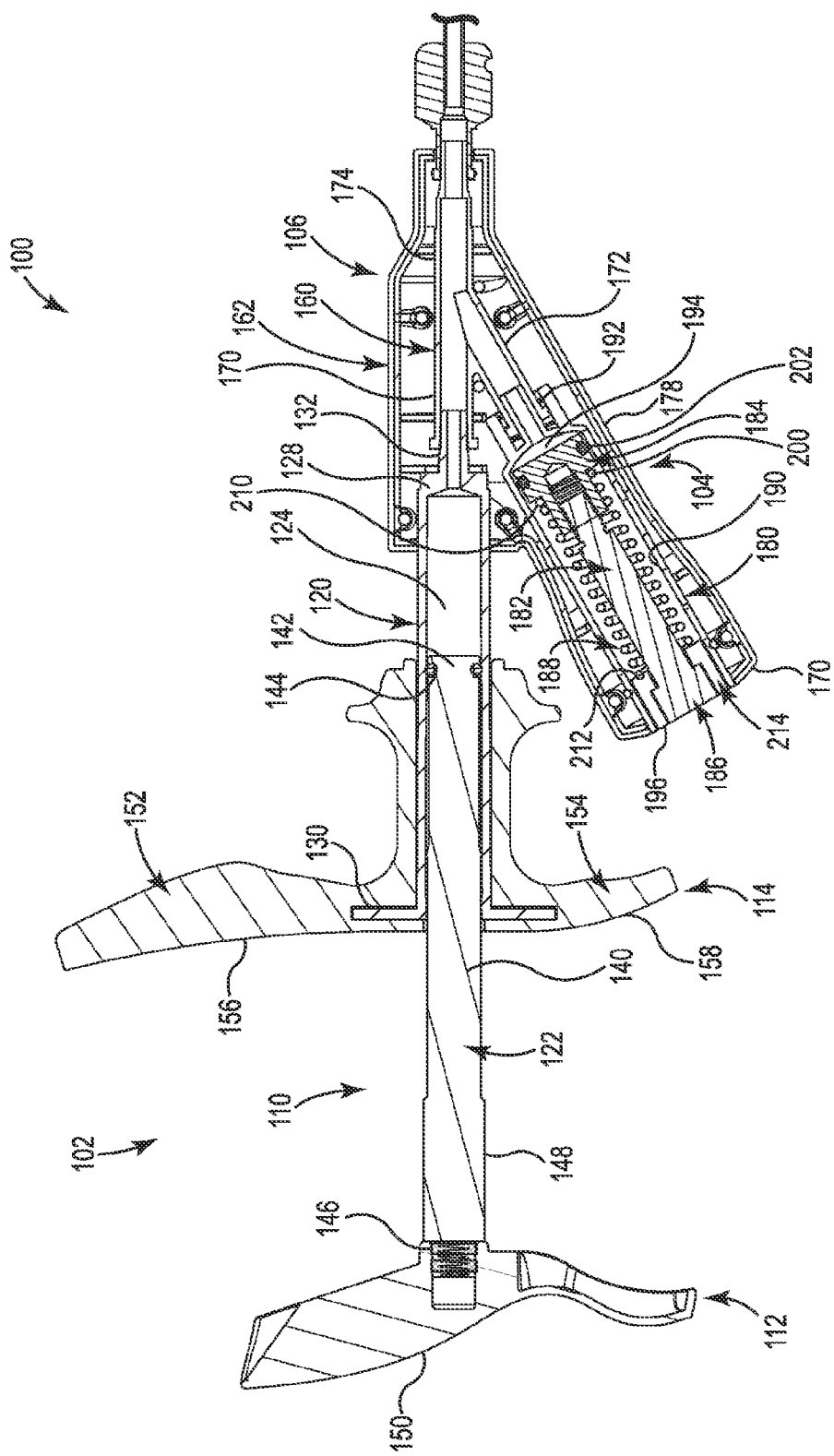
FIG. 3A is an enlarged cross-sectional side view of a portion of the inflation device of FIG. 2A in a non-alert state.

The syringe assembly 102 includes a syringe 110, an optional push handle 112 and an optional grip handle 114. The syringe 110 can be of a conventional design, and includes a barrel 120 and a plunger 122. The barrel 120 defines a chamber 124 extending between a proximal end 126 and a distal end 128. A flange 130 is optionally formed at the proximal end 126. Regardless, and as best shown in FIG. 3A, the chamber 124 is sized to maintain a volume of fluid appropriate for inflating the sinus dilation instrument balloon 26 (FIG. 1). The fluid can be dispensed from the chamber 124 via the distal end 128. The barrel 120 can form an outlet port 132 extending from the distal end 128. The outlet port 132 is open to the chamber distal end 128 and provides a smaller inner diameter (thus serving as a stop to forward movement of the plunger 122).

The plunger 122 includes a shaft 140 carrying or forming a head 142. The shaft 140 is slidably arranged with the chamber 124, including the head 142 forming a sealed relationship with the barrel 120. Thus, the head 142 can be or can carry an O-ring 144 or rubber membrane. The plunger 122 terminates at an end 146 opposite the head 142. A trailing region 148 adjacent the end 146 can have an outer diameter greater than a diameter of a remainder of the plunger 122, with this increased size serving as a stop to attempted over insertion of the plunger 122 within the barrel 120. The trailing region 148 has a diameter greater than the diameter of the chamber distal end 128 and/or the grip handle 114 (as described below) to physically prevent the plunger 122 from being overtly pressed relative to the barrel 120.

In some embodiments, the syringe 110 is a 3 mL syringe, and is configured to limit travel of the plunger 122 such that a volume of approximately 1.9 mL of inflation medium can be maintained within the chamber 124. Other sizes and volumes are also acceptable.

The handles 112, 114, where provided, promote convenient grasping and handling of the inflation device 100 by a user, as well as operation of the syringe 110. The push handle 112 is configured to be mounted to the plunger end 146 and defines or forms a contoured face 150 configured to ergonomically receive the palm and/or thumb of user's hand otherwise acting to apply a pressing force onto the push handle 112 (and thus the plunger 122). In other embodiments, the push handle 112 can assume a variety of other shapes, and can be integrally formed by the plunger 122.

The grip handle 114 is configured for assembly or molding over the barrel 120, for example forming a slot that accommodates the flange 130. The grip handle 114 defines opposing finger projections 152, 154 each forming a grasping face 156, 158 sized and shaped to ergonomically receive one or more fingers of a user's hand otherwise acting to apply a pressing force onto the push handle 112. With this optional construction, then, a user's palm is placed against the push handle face 150 while the user's finger are placed against the grip handle grasping faces 156, 158; the user's hand is then squeezed to apply a pushing force onto the push handle 112/plunger 122.

The connector assembly 106 includes a connector 160 and a cover 162. The connector 160 can assume a variety of forms and in some embodiments is a Y-connector defining first and second inlet tubes 170, 172, and an exit tube 174. The exit tube 174 is fluidly connected to the inlet tubes 170, 172, and is configured for connection to the auxiliary tubing 108. While the connector 160 has been described as being a component discrete from the syringe assembly 102 and the pressure indicator 104, in other embodiments, the connector 160 is integrally formed by or with the syringe 110 and/or the pressure indicator 104.

The cover 162 is an optional component configured to more robustly stabilize the connector 160 relative to the syringe assembly 102 and the pressure indicator 104. As generally reflected in FIG. 2B, the cover 162 forms various internal features (e.g., ribs) to which the barrel 120, the connector 160, and a component of the pressure indicator 104 are mounted. For reasons made clear below, a side 176 of an indicator region 178 of the cover 162 forms an opening 180. In other embodiments, the cover 162 can be omitted.

The mechanical pressure indicator 104 is shown in greater detail in FIGS. 3A and 3B, and includes a housing 180, a rod 182, a head 184, an indicator body 186, and a spring or other biasing device 188. In general terms, the rod 182 is slidably disposed within the housing 180, and maintains the head 184 and the indicator body 186. The spring 188 biases the rod 182 to the normal or non-alert state reflected in FIG. 3A. The mechanical pressure indicator 104 transitions to the alert state of FIG. 3B when a pressure acting upon the head 184 (in a direction opposite a bias of the spring 188) overcomes a force of the spring 188.

The housing 180 is a tubular body defining a primary chamber 190 and a port 192. A common passageway 194 extends through the chamber 190 and the port 192, and is open at a trailing end 196 of the housing 180. Further, a diameter of the passageway 194 is reduced at the port 192.

The head 184 and the indicator body 186 are connected to the rod 182 at opposite ends thereof. The head 184 includes or carries a sealing membrane 200 (along with an optional O-ring 202) having a diameter approximating a diameter of the passageway 194 within the chamber 190, and is configured to establish a fluid-tight seal against an inner wall of the housing 180 as shown. A diameter of the rod 182 is less than a diameter of the head 184. The indicator body 186 can have a diameter greater than that of the rod 182, and is sufficiently sized to be completely received within the chamber 190. The indicator body 186 can assume various forms (e.g., plastic) and in some embodiments is brightly colored (e.g., red). The indicator body 186 is, in some embodiments, integrally formed with the rod 182.

The spring 188 is selected to have a known spring force constant as described below. The spring 188 is slidably disposed about the rod 182, and is attached at a first end 210 to the head 184. An opposing, second end 212 of the spring 188 is robustly mounted within the chamber 190. For example, the mechanical pressure indicator 104 can include an end cap 214 mounted within the passageway 194 adjacent the trailing end 196 and providing a reduced diameter surface against which the second end 212 of the spring 188 is maintained. As best shown in FIG. 3B, the end cap 214 forms an internal bore 216 within which the indicator body 186 is slidably received. For reasons made clear below, with constructions in which the housing 180 is transparent or nearly transparent, the end cap 214 can be opaque or otherwise configured to visually obscure the indicator body 186 when located within the end cap 214.

Upon final assembly, the spring 188 biases the head 184 toward the port 192, with the head 184 and/or the sealing member 200 establishing a fluid seal with the chamber 190. A length of the rod 182, the head 184 and the indicator body 186 is such that in the normal, non-alert state or condition of FIG. 3A, the indicator body 186 is located entirely within the housing 180, and is thus exteriorly hidden from view (e.g., one or both of the housing 180 and the end cap 214 are opaque thus obscuring the indicator body 186). Conversely, when the head 184 is forced rearward within the chamber 190 as described below, at least a portion of the indicator body 186 is located exterior the housing 180 (and the cover 162) in the alert state of FIG. 3B, and thus is visible to a user from an exterior of the housing 180.

Construction of the inflation device 100 includes assembling the connector first inlet tube 170 to the syringe outlet port 132, and the second inlet tube 172 to the pressure indictor port 192. Thus, the connector 160 fluidly connects the syringe 110 with the pressure indicator 104, with the outlet tube 174 being fluidly open to the fluid or pressure of (or generated by operation of) the syringe 110. The cover 162, where provided, is assembled to the connector 160, the barrel 120 and the housing 180 as shown. As reflected by FIGS. 2A and 2B, during use of the inflation device 100 with the sinus dilation instrument 22 (FIG. 1), the connector outlet tube 174 is fluidly connected to the balloon 26 (FIG. 1), for example via an inflation lumen (not shown) of the sinus dilation instrument and the auxiliary tubing 108. A closed inflation system or path is formed between the inflation device 100 and the balloon 26, and fluid delivered from and/or pressure generated by the inflation device 100 causes the balloon 26 to expand. It will be understood that when dilating a sinus ostium, the structure against which the balloon 26 is placed will resist expansion of the balloon 26, thus creating an elevated pressure within the inflation system. As the user exerts an increased force on the plunger 122 to effectuate desired balloon inflation (e.g., transitions from the arrangement of FIG. 3A to the arrangement of FIG. 3B), the inflation system pressure will further increase. It may be desirable to alert a user when the inflation system pressure has reached a certain level. With this in mind, the mechanical pressure indicator 104 is fluidly exposed to the inflation system pressure, with the pressure exerting a force on the head 184 in a direction opposite a biasing force of the spring 188. At inflation system pressures below the spring force constant of the spring 188, the force generated by the spring 188 exceeds the force applied on the head 184 by the inflation system pressure, and the pressure indicator 104 remains in the non-alert state of FIGS. 2A and 2B (i.e., the indicator body 186 remains hidden within the housing 180 and/or end cap 214). When the inflation system pressure exceeds the force applied by the spring 188, the head 184, and thus the rod 182 and the indicator body 186, are displaced in a rearward direction to the alert state of FIG. 3B. The displacement locates the indicator body 186 outside of the housing 180 where it is easily seen or visually perceived by a user.

With the above explanations in mind, and with specific reference to FIGS. 3A and 3B, a spring force constant can be selected for the spring 188 that corresponds with a desired, target inflation system pressure. Stated otherwise, based upon one or more factors such as expected sinus dilation anatomical constraints, system component limitations (e.g., burst strength of the sinus dilation balloon 26 (FIG. 1)), etc., a target inflation system pressure can be determined and the spring 188 is selected or constructed to exhibit a spring force constant that is approximately equal to the force associated with the determined target inflation system pressure. In related embodiments, the spring force constant of the spring 188 in combination with a preload force established upon the spring 188 upon assembly within the housing 180 is selected such that the indicator 104 transitions to the alert state at the predetermined inflation system pressure target limit. Regardless, during use, once the indicator body 186 becomes visible (e.g., the alert state of FIG. 3B), the user readily understands that the desired target inflation system pressure has been reached and that no additional force should be applied to the plunger 122. In some embodiments, an interface between the indicator body 186 and the end cap 214 (or other component of the indicator 104) is such that a tactile and/or audible "click" is generated as the indicator body 186 displaces from the end cap 214. For example, a slight frictional interface can be established with movement of the indicator body 186 producing a tactile and/or audible "click" (or other noise) that can be felt and/or heard by a user otherwise handling the inflation device 100. The optional tactile attribute in transitioning from the non-alert state to the alert state can be beneficial in low light environments. By way of example, a balloon pressure of approximately 2 ATM is typically required to break paranasal bone and other tissue as part of a sinus ostium dilation procedure. Successful sinus dilation normally does not require a balloon pressure greater than 10 ATM, and sinus dilation procedures conventionally specify an upper limit of 12 ATM. Balloon pressures (or attempted balloon pressures) well above 12 ATM are unnecessary and may lead to patient complications, instrument failure, or both. In some embodiments, then, the inflation device 100 (as well as other embodiment inflation devices described below) is configured to transition to the alert state when the inflation system pressure reaches about 10 ATM+/−1 ATM, in other embodiments about 12 ATM+/−1 ATM.

In some embodiments, a volume of the mechanical pressure indicator 104 is significantly larger than that of the syringe 110. Stated otherwise, the volume of the indicator chamber 190 (FIG. 3B) is greater than a volume of the syringe chamber 124. With this construction, when the desired inflation system pressure is reached, displacement of the head 184 effectively absorbs the additional fluid displaced by the syringe plunger 122, and limits the amount of additional pressure that can be produced, thus reducing the risk of an accidental over-pressure condition. In related embodiments, a stroke length of the syringe 110 (i.e., longitudinal length of the plunger 122 from the head 142 to the trailing region 148) can be selected so as to not exceed an expected distance of travel otherwise needed for most sinus dilation inflation procedures. In some embodiments, the inflation device 100 is configured such that the pressure indicator 104 transitions to the alert state at an inflation system pressure of 10 ATM+/−1 ATM, and prevents the syringe 110 from being operated to create an inflation system pressure in excess of 12 ATM+/−1

ATM. In other, related embodiments, the indicator body 186 (or any other structure specifically included to provide a visual "warning" to a user) can be omitted, with the pressure indicator 104 beneficially providing the pressure accumulation/limits described above. With these constructions, the pressure indicator device 104 can alternatively be referred to as an "over pressure controller" in that no overt "indication" of system pressure is provided to a user.

With embodiments in which the inflation device 100 is used in performing a sinus dilation procedure, methods in accordance with principles of the present disclosure include selecting a sinus dilation instrument (e.g., the sinus dilation instrument 22 of FIG. 1) appropriate for accessing the paranasal target site. The tubing 108 is fluidly connected to the instrument's balloon 26 (FIG. 1) and the connector assembly 106 (as shown, for example, in FIG. 2B). The syringe 110 can be pre-loaded with the inflation medium, or the user can fill the syringe 110 with a desired volume of the inflation medium prior to connection with the tubing 108. Regardless, the balloon 26 is initially deflated, the syringe assembly 102 is in the loaded state of FIG. 3A, and the pressure indicator 104 is in the non-alert state of FIG. 3A. The sinus dilation instrument 22 is manipulated by a user to locate the balloon 26 at the target site, for example by directing the probe 24 through the patient's nostril and along the desired paranasal passageways. Once the balloon 26 has been located at the paranasal target site, the inflation device 100 is operated to expand the balloon 26. In other embodiments, the tubing 108 is fluidly connected to the balloon 26 after first directing the balloon to the paranasal target site. Expansion or inflation of the balloon 26 occurs as the plunger 122 is pressed by the user, forcing the inflation medium into the tubing 108 and increasing pressure within the inflation system. Once the inflation system pressure reaches the predetermined level (e.g., 10 ATM), the pressure indicator 104 self-transitions from the non-alert state of FIG. 3A to the alert state of FIG. 3B. The indicator body 186 becomes readily visible to the user, alerting the user that the target inflation system pressure has been reached. A tactile and/or audible alert is also generated. Knowledge that the target inflation system pressure has been reached confirms for the user that a desired re-shaping of the paranasal target site has occurred (e.g., necessary breakage of nasal bone and other tissue). The user can then deflate the balloon 26 by operating the syringe 110 in the opposite direction, and end the procedure. Alternatively, the user may decide to further increase the inflation system pressure by applying additional force on to the plunger 122. The inflation device 100 will permit the inflation system pressure to increase beyond the target pressure (i.e., after transitioning to the alert state, the inflation system pressure can be further increased), but only up to a maximum limit permitted by a stroke length of the plunger 122 and pressure relief accommodated by the pressure indicator 104 (e.g., 12 ATM).

Figure 4A:
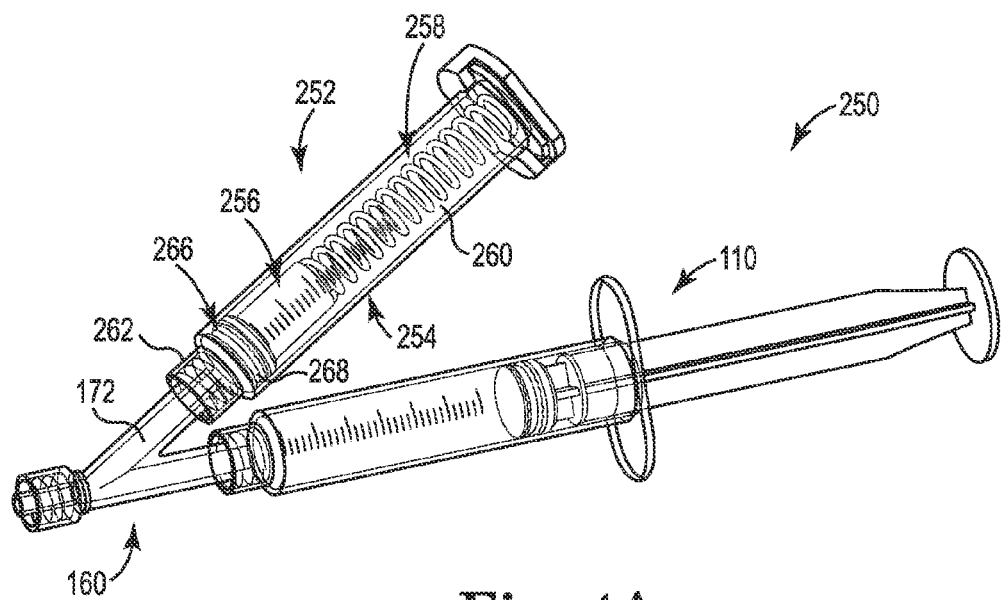
FIG. 4A is a perspective view of another inflation device in accordance with principles of the present disclosure with components removed and in a non-alert state.
Figure 4B:
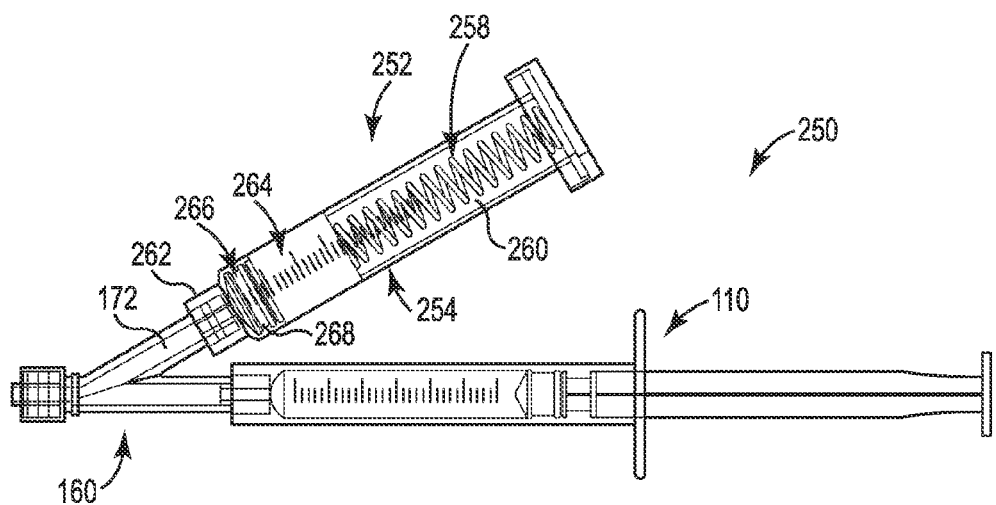
FIG. 4B is a side view of the inflation device of FIG. 4A.

Another, related embodiment inflation device 250 is shown in FIGS. 4A and 4B, and includes the syringe 110 and the connector 160 as described above, and a mechanical pressure indicator or over pressure controller 252. The mechanical pressure indicator 252 is akin to the indicator 104 (FIG. 2B) previously described, and generally includes a housing 254, an indicator body 256 (visible in FIG. 4A), and a spring or other biasing device 258. The indicator body 256 and the spring 258 are disposed within a primary chamber 260 defined by the housing 254. The primary chamber 260 is fluidly open at a port 262 otherwise configured for coupling to the second inlet tube 172 of the connector 160. A shield 264 (omitted from the view of FIG. 4A to illustrate the indicator body 256, but shown in FIG. 4B) is formed on or carried by the housing 254 adjacent the port 262. The shield 264 is opaque, whereas a remainder of the housing 254 is transparent or substantially transparent (e.g., not less than 90% transparent).

The indicator body 256 is slidably disposed within the primary chamber 260. In some embodiments, the indicator body 256 is attached to or carried by a head 266 disposed within the primary chamber 260 and including a sealing member 268 that is fluidly sealed against an interior of the housing 254. Regardless, the spring 258 is disposed within the housing 254, and establishes a biasing force, either directly or indirectly, upon the indicator body 256. For example, an end cap 270 can be secured over the primary chamber 260 and against which the spring 258 is rigidly secured. An opposite end of the spring 258 is fixed to the head 266 (or alternatively, directly to the indicator body 256). The spring 258 biases the indicator body 256 to the non-alert state as shown in FIGS. 4A and 4B in which the indicator body 256 is within the shield 264 and thus is not visible from an exterior of the pressure indicator 250 (as reflected in FIG. 4B).

Figure 5:
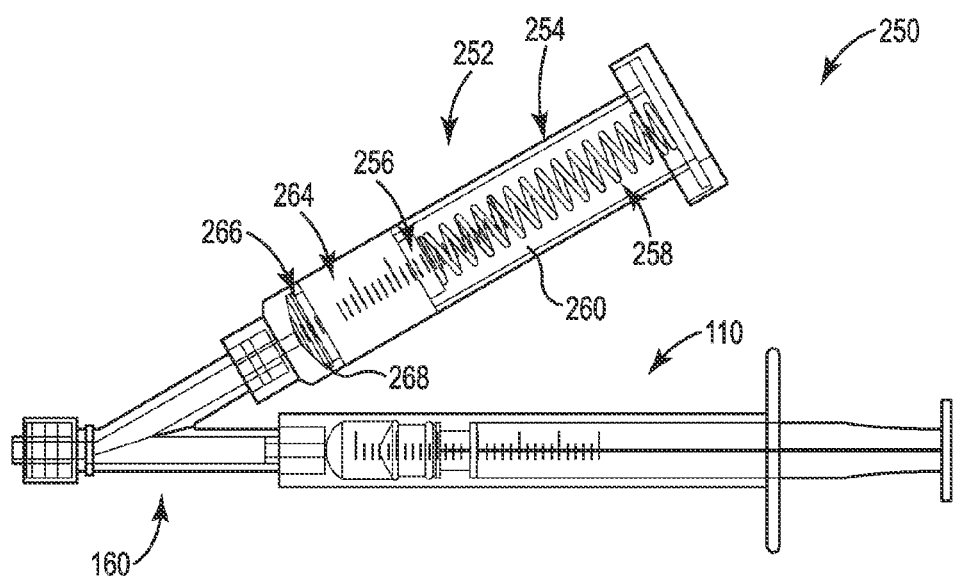
FIG. 5 is a side view of the inflation device of FIG. 4A in an alert state.

During use, a spring force constant of the spring 258 (and/or a preload force imparted on the spring 258) correlates with a desired target inflation system pressure for the inflation device 258. As with the embodiments described above, as an internal pressure within the inflation system is increased (i.e., the syringe 110 is operated to inflate the sinus dilation instrument's balloon), a force is exerted against the head 266 in a direction opposite the biasing force of the spring 258. As the applied pressure increases, the spring 258 is caused to compress. When a predetermined target inflation system pressure is reached, the indicator body 256 is displaced rearwardly away from the shield 264 and becomes visible beyond the shield 264 as shown in FIG. 5. In this alert state of the pressure indicator 252, the user is immediately apprised that the target inflation system pressure has been reached. A tactile and/or audible "click" may also be generated in transitioning from the non-alert state to the alert state.

Figure 6:
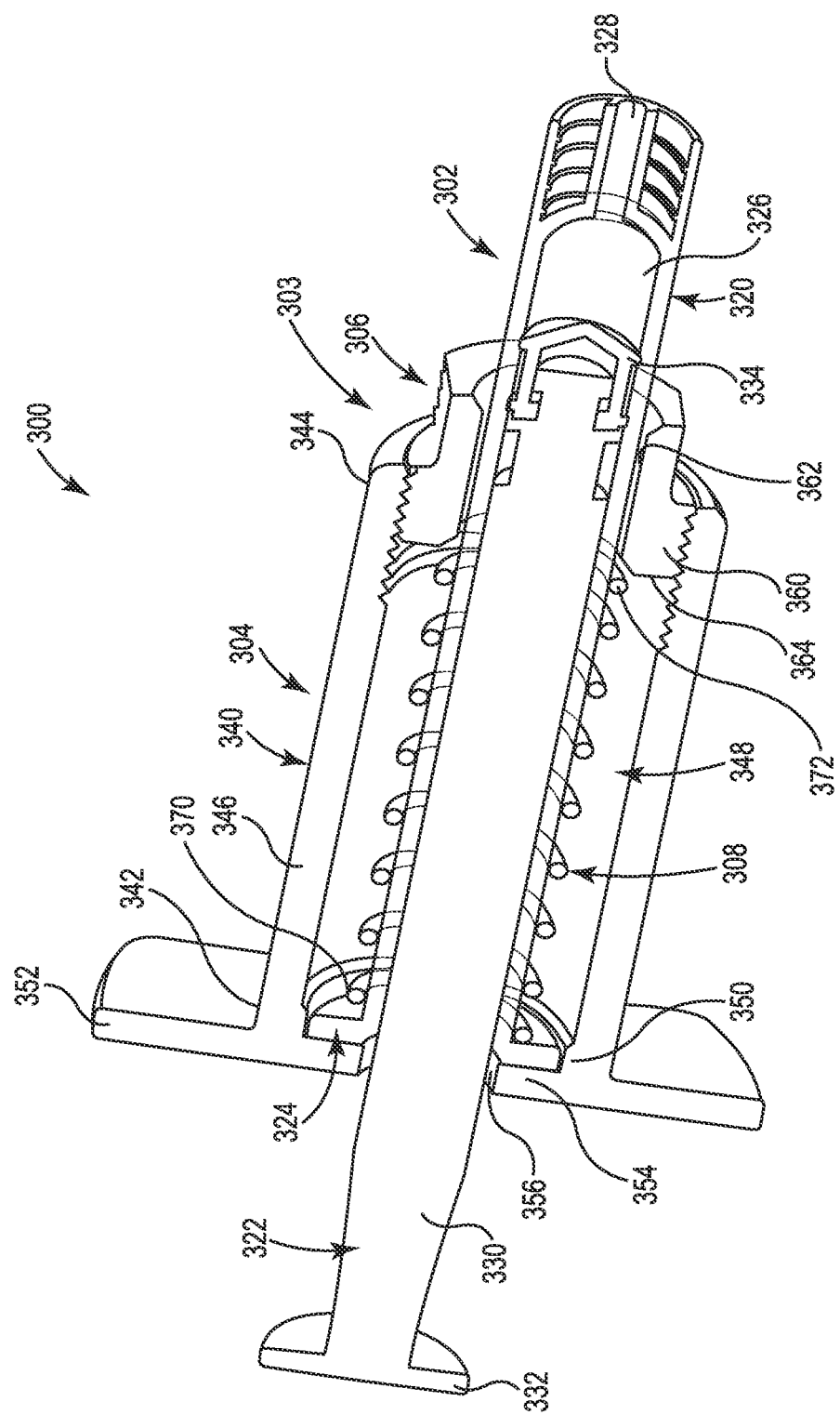
FIG. 6 is a cross-sectional view of another inflation device in accordance with principles of the present disclosure.

Another embodiment inflation device 300 in accordance principles of the present disclosure is shown in FIG. 6. The inflation device 300 comprises a syringe 302 and a pressure indicator or over pressure controller 303 including a housing 304, an end cap 306, and a spring or other biasing device 308. In general terms, the spring 308 retains the syringe 302 relative to the housing 304 at applied forces below a predetermined level. Once the force applied to the syringe 302 exceeds the spring force, the syringe 302 disengages from a feature of the housing 304 to generate a tactile and/or audible "click".

The syringe 302 can have a conventional form, and includes a barrel 320 and a plunger 322. The barrel 320 terminates at a flange 324, and defines a chamber 326 fluidly open to a dispensing channel 328. The plunger 322 includes a shaft 330 maintaining or forming a head 332 and a sealing member 334 at opposite ends thereof. The shaft 330 is slidably disposed within the chamber 324, with the sealing member 334 forming a liquid-tight seal against the barrel 320.

The housing 304 includes a housing body 340 extending between opposing, first and second ends 342, 344. The housing body 340 is tubular, having a wall 346 defining an interior containment region 348. A diameter of the interior region 348 can be relatively uniform, sized to slidably maintain the spring 308 and the syringe barrel 320 as described below. Regardless, a shoulder 350 is formed as a radially inward projection from the wall 346 at the first end 342. The shoulder 350 represents a reduction in diameter of the inner region 348. In this regard, a diameter of the shoulder 350 approximates (e.g., is slightly less than) an outer diameter of the barrel flange 324 such that frictional engagement between the flange 324 and the shoulder 350 is provided upon final assembly.

A finger grip 352 is formed by, or attached to, the housing body 340 at the first end 342 as a radially outward projection from the wall 346. A platform 354 extends radially inwardly from the wall 346 at the first end 342 opposite the finger grip 352, and forms a central aperture 356 sized to slidably receive the plunger shaft 330 (i.e., a diameter of the aperture 356 is slightly greater than a diameter of the shaft 330). An inner diameter of the platform 354 is less than a diameter of the plunger head 332 for reasons made clear below.

The end cap 306 is a ring-shaped body defining a ledge 360 and a guide passage 362. The ledge 360 forms an engagement surface 364 sized and shaped to receive a portion of the spring 308. The guide passage 362 has a diameter slightly greater than a diameter of the syringe barrel 320. With this construction, the barrel 320 can be loosely received within the guide passage 362 such that the barrel 320 slides freely relative to the end cap 306 during use. Finally, the end cap 306 is configured for mounting to the second end 344 of the housing 304. In one non-limiting example, the end cap 306 and the housing wall 346 form complimentary threads. With these and other mounting formats, a longitudinal distance between the ledge 360 and the housing first end 342 can be selectively altered by a user.

The spring 308 can be a coil spring extending between opposing, first and second ends 370, 372. An inner diameter of the spring 308 is sized to slidably receive the syringe barrel 320. Further, a diameter at the first end 370 is less than a diameter of the barrel flange 324, and a diameter at the second end 372 is less than a diameter of the end cap engagement surface 364. The spring 308 can have a variety of other forms exhibiting a biasing force and facilitating operation of the inflation device 300 as described below.

Assembly of the inflation device 300 includes disposing the spring 308 about the syringe barrel 320, with the spring first end 370 abutting the flange 324. The syringe 302/spring 308 is loaded into the housing 304. In particular, with the end cap 306 removed from the housing 304, the syringe barrel 320/spring 308 is inserted into the interior region 348. The flange 324 is located against the platform 354, and is frictionally engaged by the shoulder 350. Where necessary, the plunger 322 can then be loaded into the barrel chamber 326 via the aperture 356. Regardless, the end cap 306 is placed over the barrel 320 (e.g., the barrel 320 is slidably located within the guide passage 362), and mounted to the housing 304. In this regard, as the ledge 360 is moved toward the housing first end 342, the spring second end 372 comes into abutment with the engagement surface 364. Recalling that the spring first end 370 abuts the flange 324 and that the flange 324 abuts the housing platform 354, with further movement of the end cap 306 toward the housing first end 342 (e.g., threaded engagement between the housing 304 and the end cap 306 mentioned above), the spring 308 is placed into compression (i.e., a preloaded force is created in the spring 308). The preload force thus established in the spring 308 can be selected by a user in accordance with a desired target inflation system pressure value as described above.

Prior to use, an inflation medium (not shown) is loaded into the syringe chamber 326, and the dispensing channel 328 is fluidly connected to the dilation instrument of the present disclosure (e.g., auxiliary tubing 108 (FIG. 2A) fluidly connects the dispensing channel 328 to the sinus dilation instrument's balloon 26 (FIG. 1)). As a result, a closed inflation system or path is established between the inflation device 300 and the sinus dilation instrument balloon 26. To effectuate inflation of the balloon 26, the user grasps the inflation device 300 at the finger grip 352 and applies a pressing force onto the plunger head 332 (e.g., with the user's fingers placed against an underside of the finger grip 352 and the user's thumb placed against the plunger head 332, a pressing force is applied to the plunger head 332 by squeezing the thumb and fingers toward one another, it being understood that a corresponding pulling force is reactively applied to the finger grip 352). The pressing force is transferred on to the plunger sealing member 334 and thus onto the inflation fluid contained within the chamber 326. As the plunger sealing member 334 moves toward the dispensing channel 328, a volume of the chamber 326 (and thus of the entire inflation system) is reduced, resulting in an increase in inflation system pressure and thus inflation of the balloon 26. As the plunger 322 is initially pressed and inflation system pressure is increased, there is no relative movement between the syringe barrel 320 and the housing 304; so long as the force applied to the plunger head 332 is less than or equal to the preload force on the spring 308, the spring 308 biases the barrel 320 to the initial or non-alert state shown in which the flange 324 is held within the shoulder 350. When the force applied to the plunger head 332 exceeds the spring preload force, the barrel 320 is caused to move away from the housing first end 342, with the flange 324 disengaging from the shoulder 350. The flange 324/shoulder 350 can be configured such that with this disengagement, a tactile and/or audible "click" is generated. By setting the spring preload force to be commensurate with a desired target inflation system pressure level (e.g., 10 ATM), then, the inflation device 300 alerts a user that the desired target inflation system pressure has been reached via the tactile click.

Figure 7A:
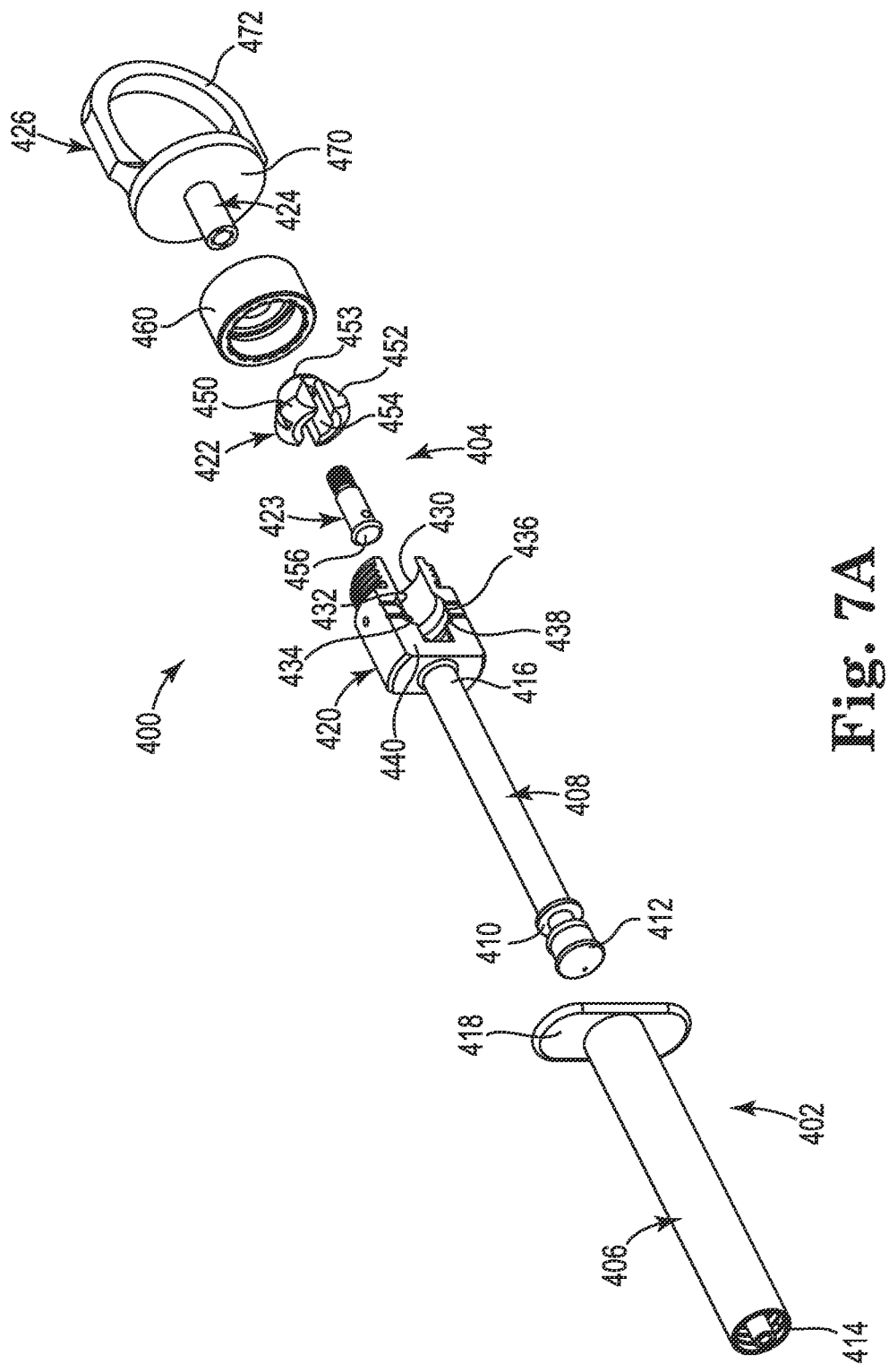
FIG. 7A is an exploded perspective view of another inflation device in accordance with principles of the present disclosure.
Figure 7B:
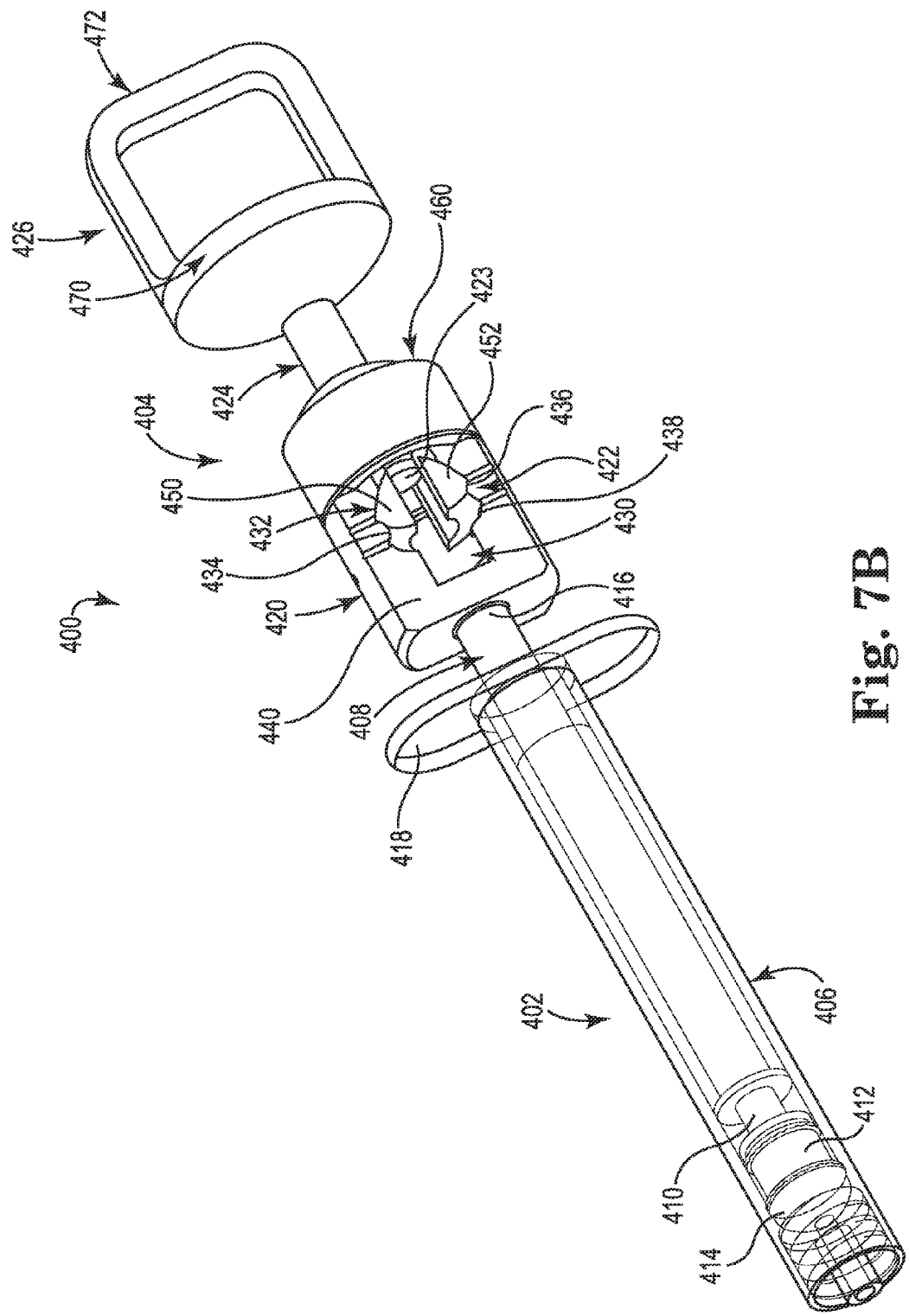
FIG. 7B is a perspective view of the inflation device of FIG. 7A in a non-alert state.
Figure 7C:
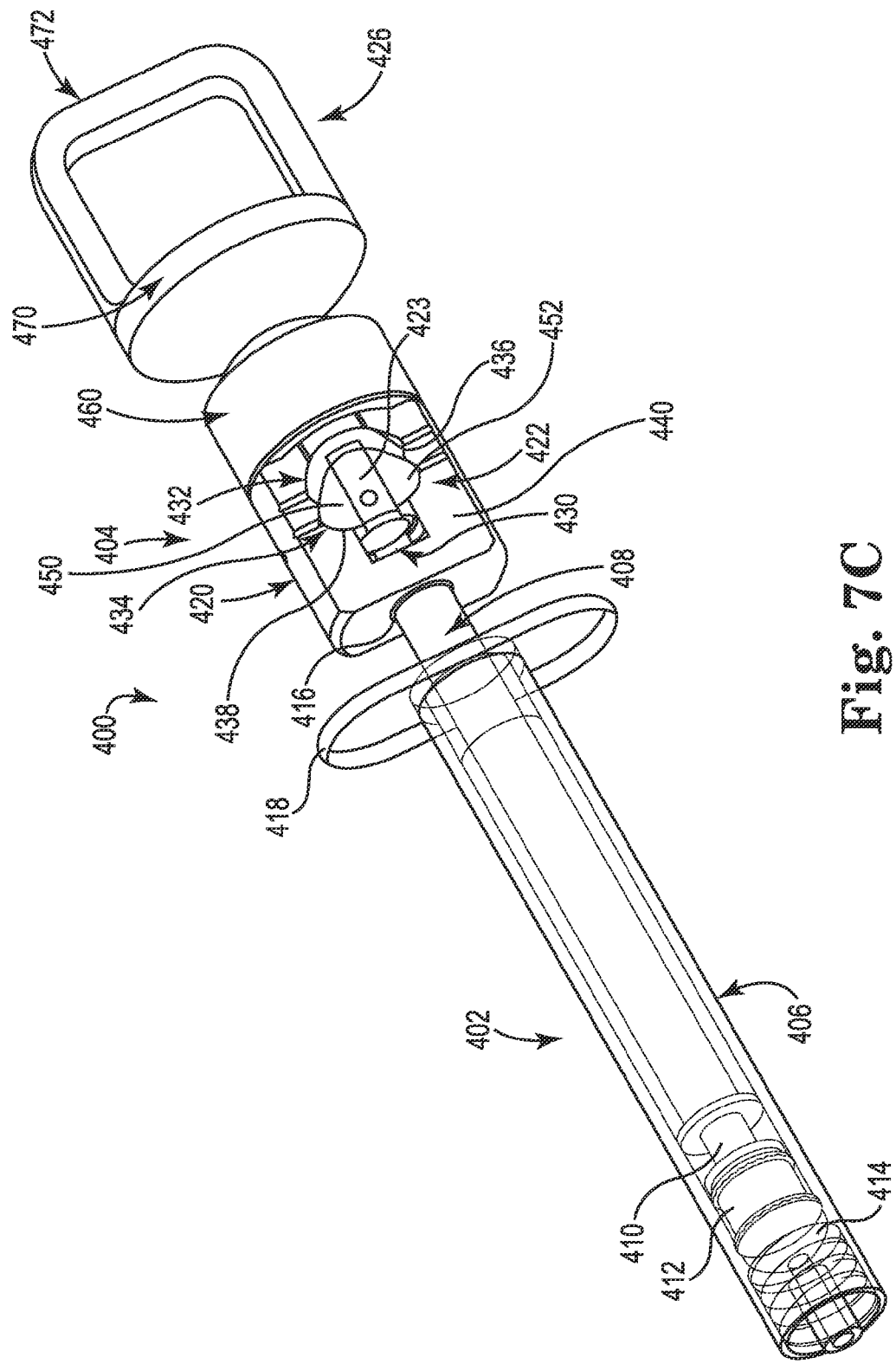
FIG. 7C is a perspective view of the inflation device of FIG. 7A in an alert state.

Another inflation device 400 in accordance with principles of the present disclosure is shown in FIGS. 7A-7C, with FIG. 7B illustrating a non-alert state and FIG. 7C illustrating an alert state. The inflation device includes a syringe 402 and a pressure indicator or over pressure controller 404. The syringe 402 can assume conventional format, and includes a barrel 406 and a plunger 408. The plunger 408 forms a first end 410 carrying a seal member 412 that is slidably disposed within a chamber 414 of the barrel 406. An opposite, second end 416 of the plunger 408 is assembled to, or is part of, the pressure indicator 404 as described below. The barrel 406 can include a flange 418 or other structure (e.g., finger loops) at which a user force is conventionally applied during use.

The pressure indicator 404 includes a support block 420, a coupling structure 422, a slide body 423, a rod 424 and a handle 426. In general terms, the support block 420 is attached to the plunger second end 416. The coupling structure 422 and the slide body 423 maintain the rod 424 (and thus the handle 426) relative to the plunger 408 such that a pressing force applied at the handle 426 is transferred to the plunger 408. When the pressing force applied to the handle 426 exceeds a predetermined level, the coupling structure 422 moves relative to the support block 420, generating a tactile and/or audible "click".

The support block 420 can be integrally formed with the plunger 408, or can be formed separately and affixed to the plunger second end 416. Regardless, the support block 420 forms a central bore 430 defining first and second capture zones 432, 434. As shown, the capture zones 432, 434 are characterized as having a radially increased width (as compared to a remainder of the bore 430) and are sized and shaped in accordance with corresponding features of the coupling structure 422 as described below. In this regard, each of the capture zones 432, 434 is defined by a leading edge 436, 438, respectively, having a decreasing radial width. In some embodiments, the support block 420 is configured to deform at the capture zones 432, 434 at certain applied force levels. In some embodiments, the bore 430 is open at opposing sides of the support block 420 (one of which is visible in the views and designated at 440) to permit viewing of a location of the coupling structure 422 within the bore 430.

The coupling structure 422 can assume a variety of forms and in some embodiments can include opposing spring fingers 450, 452 extending from a collar 453 and separated by a channel 454 (as seen in FIG. 7A). The coupling structure 422 is configured to selectively engage with the support block 420 within each of the first and second capture zones 432, 434. For example, with embodiments in which the coupling structure 422 includes the opposing spring fingers 450, 452, the spring fingers 450, 452 each have a perimeter shape corresponding with a shape of a corresponding segment of the capture zones 432, 434. The spring fingers 450, 452 naturally assume an outwardly biased construction such that when the fingers 450, 452 are aligned with one of the capture zones 432, 434, the fingers 450, 452 self-bias into engagement with the capture zone 432, 434. In the engaged condition, the fingers 450, 452 bear against the leading edge 436, 438 of the corresponding capture zone 432, 434. The channel 454 is sized to slidably receive the slide body 423. The coupling structure 422 can be configured to exhibit deflection or compression at certain applied force levels, for example by the fingers 450, 452 being configured to inwardly deflect relative to one another for reasons made clear below.

The side body 423 defines a head 456 and is sized to be received within the channel 454 formed between the fingers 450, 452. The slide body 423 is further configured for attachment to the rod 424. Sliding engagement of the slide body 423 with the coupling structure 422 can be achieved in various manners such that the slide body 423 is moveable relative to coupling structure 422 between the retracted position of FIG. 7B and the forward position 7C. As a point of reference, in the retracted position of FIG. 7B, the head 426 abuts the collar 453 such that a refraction force on the handle 426/slide body 423 is transferred directly on to the coupling structure.

The rod 424 is attached to the handle 426 and the slide body 423. The side body 423 thus effectively serves as a smaller diameter extension of the rod 424. While the slide body 423 is sized to slide within the channel 454, the rod 424 has an enlarged outer dimension and cannot pass through the collar 453. In the forward position of FIG. 7C, then, the rod 424 bears against the coupling structure 422 such that an advancement force on the handle 426/rod 424 is transferred directly to the collar 453. In some embodiments, the pressure indicator 404 can further include a hub 460 that supports and guides movement of the rod 424 relative to the support block 420.

The handle 426 can assume any form conducive to handling by a user's hand or fingers in a manner facilitating the user applying a pressing force on to the inflation device 400. Thus, the handle 426 optionally forms or includes a plate 470 and a frame 472. The plate 470 is sized and shaped to receive a user's thumb, with the frame 472 adapted to assist in maintaining positive contact between the user's thumb and the plate 470. Other forms for the handle 426 are equally acceptable.

In the non-alert state of FIG. 7B, the syringe chamber 414 is loaded with an inflation medium (not shown), and the pressure indicator 402 is arranged such that the coupling structure 422 is engaged within the first capture zone 432. A squeezing force is applied by a user at the handle 426 and the flange 418. The pressing force applied at the handle 426 causes the slide body 423 to slide or advance within coupling structure 422 until the rod 424 contacts the collar 454. The slide body 423 is transitioned to the second position (FIG. 7C); however, the coupling structure 422 remains within the first capture zone 432. Continued application of the force at the handle 426 is transferred to the support block 420 via the coupling structure 422 and the rod 424. At applied forces below a predetermined level, the coupling structure 422 remains engaged within the first capture zone 432, with the applied pressing force being transferred to the support block 420 at the coupling structure 422/leading edge 436 interface. This pressing force is directly transposed on to the plunger 408, causing inflation medium to be dispensed from the chamber 414.

As pressure within the inflation system begins to increase, the pressing force applied to the handle 426 will also increase. At inflation system pressures below a predetermined level, the corresponding pressing force is insufficient to cause the coupling structure 422 to disengage from the first capture zone 432. However, when the inflation system pressure exceeds the predetermined level, the corresponding pressing force, as applied to the coupling structure 422, causes the pressure indicator 404 to transition from the non-alert state of FIG. 7B to the alert state of FIG. 7C. More particularly, in transitioning from the non-alert state, the coupling structure 422 causes the support block bore 430 to slightly expand at the leading edge 436 of the first capture zone 432 (e.g., the head 456 of the slide body 423 prevents the fingers 450, 452 from deflecting toward one another, and the support block 430 deforms). With continued forward movement, the coupling structure 422 disengages from the first capture zone 432 and then self-engages within the second capture zone 434 as shown in FIG. 7B. As the coupling structure 422 is brought into engagement with the second capture zone 434, a tactile and/or audible "click" is generated. This tactile snapping action (and/or visual confirmation that the coupling structure 422 has moved to the second capture zone 434) readily informs the user that the inflation system pressure has risen to a predetermined level. While the user can continue to apply a pressing force on to the handle 426 (with this force being transposed on to the support block 420/plunger 408 via the coupling structure 422/leading edge 438 interface), the user will be advised that the predetermined target inflation system pressure has been obtained.

By selecting the materials of the support block 420 and the coupling structure 422, as well as the form of interface there between, the inflation device 400 can be configured to transition to the alert state at a particular inflation system pressure (e.g., 10 ATM). The inflation device 400 can be re-set by retracting the handle 426. The slide body 423 retracts from between the fingers 450, 452 allowing the fingers 450, 452 to readily deflect with further retraction of the coupling structure 422 relative to the support block 420, and subsequently engage within the first capture zone 432.

The inflation devices of the present disclosure provide a marked improvement over previous designs, including those conventionally employed with balloon sinus dilation procedures. For example, inflation devices of the present disclosure are characterized by the absence of a conventional dial pressure gauge. The simplified format of the disclosed inflation devices is, as compared to conventional designs, easier and more intuitive to use, less costly, and generates less waste as a disposable device. The cost-effective inflation devices are capable of providing necessary balloon inflation and target pressure level "warnings" and/or control. The inflation devices of the present disclosure can be used with a variety of differently-constructed sinus dilation instruments, such as those with a rigid probe or a flexible catheter. Further, while the inflation devices have been described as being useful with sinus dilation procedures and instruments, a wide variety of other surgical balloon procedures and instruments can also benefit from the disclosed inflation devices that may or may not involve the paranasal sinuses.

Although the present disclosure has been described with reference to preferred embodiments, workers skilled in the art will recognize that changes can be made in form and detail without departing from the spirit and scope of the present disclosure. For example, while inflation devices of the present disclosure have been described as incorporating a spring into the corresponding pressure indicator to generate a desired biasing force, other biasing or compensation configurations are also envisioned. The mechanical spring can be replaced by a flexible bellows assembly, or a solenoid or electrical transducer. Also, while the inflation devices of the present disclosure have been described as including a pressure indicator configured to provide at least a visual alert to a user when an inflation system target pressure has been reached, in other embodiments, any of the indicators of the present disclosure can be modified to not generate a direct visual indication of pressure level yet still provide beneficial pressure accumulation/limit as described.

What is claimed is:

1. An inflation device for selectively inflating a balloon of surgical instrument, the device comprising:
    a syringe including a plunger slidably disposed within a barrel;
    a connector for fluidly connecting an outlet of the syringe with a surgical instrument balloon to establish a closed inflation system between the syringe and an interior of the balloon; and
    a mechanical pressure indicator associated with the syringe and configured to transition from a non-alert state to an alert state when a pressure of the inflation system has reached a predetermined level.

2. The device of claim 1, wherein the pressure indicator is further configured to regulate operation of the syringe once the predetermined level has been reached.

3. The device of claim 1, wherein the device is characterized by the absence of a pressure gauge.

4. The device of claim 1, wherein the pressure indicator includes:
    a rod slidably disposed within a housing;
    wherein an interior of the housing is fluidly connected to the syringe outlet;
    a head assembled to a first end of the rod; and
    a spring biasing the head to a first position within the housing;
    wherein the pressure indicator is configured such that a pressure of the inflation system acts upon the head in a direction opposite a biasing force of the spring.

5. The device of claim 4, wherein the pressure indicator is further configured such that the head transitions toward a second position as a pressure acting on the head overcomes a biasing force of the spring.

6. The device of claim 5, wherein the pressure indicator further includes an indicator body assembled to the rod, and further wherein the pressure indicator is configured such that the indicator body is not visible from an exterior of the housing in the first position and is visible in the second position, the second position corresponding with the alert state and being indicative of the inflation system pressure having reached the predetermined level.

7. The device of claim 6, wherein the indicator body is assembled to a second end of the rod opposite the first end.

8. The device of claim 7, wherein the housing defines an inlet side and an outlet side, and further wherein the head is located adjacent the inlet side, and even further wherein the indicator body is within the housing in the non-alert state and at least a portion of the indicator body projects outside of the outlet side in the alert state.

9. The device of claim 6, wherein the indicator body is assembled to the rod adjacent the head.

10. The device of claim 9, wherein the pressure indicator further includes a shield disposed within the housing, the indicator body being within the shield in the non-alert state and at least a portion of the indicator body being outside of the shield in the alert state.

11. The device of claim 6, wherein the spring has a spring preload corresponding with the predetermined pressure level.

12. The device of claim 1, wherein the pressure indicator includes:
    a housing disposed about a portion of the barrel; and
    a spring disposed between an end of the barrel and the housing;
    wherein the pressure indicator is configured such that the end of the barrel disengages from the housing once a pressure of the inflation system exceeds a biasing force of the spring.

13. The device of claim 12, wherein the end of the barrel disengages from the housing at the predetermined level.

14. The device of claim 12, wherein the pressure indicator is configured to generate a tactile click as the end of the barrel disengages from the housing.

15. The device of claim 1, wherein the pressure indicator includes:
    a support block attached to the plunger;
    a coupling structure selectively engaged with the support block; and
    a handle assembly connected to the coupling structure;
    wherein the pressure indicator is configured such that a location of the coupling structure relative to the support block changes when a pressure of the inflation system exceeds a predetermined level.

16. The device of claim 15, wherein the coupling structure includes a pair of spring fingers selectively engaged within a bore defined by the support block.

17. The device of claim 1, wherein the syringe has a stroke length corresponding to a desired inflation pressure of the balloon.

18. An inflation device for selectively inflating a balloon of a surgical instrument, the device comprising:
    a syringe including a plunger slidably disposed within a barrel;
    a connector for fluidly connecting an outlet of the syringe with a surgical instrument balloon to establish a closed inflation system between the syringe and an interior of the balloon; and
    an over pressure controller associated with the syringe and configured to regulate inflation system pressure once a pressure of the inflation system has reached a predetermined level.

19. A method of dilating a region of a patient's nasal sinus system, the method comprising:
    manipulating a sinus dilation instrument to direct a balloon, in a deflated state, of the sinus dilation instrument along intranasal sinus passageways of the patient to a nasal sinus target site;
    fluidly connecting an inflation device to the balloon, the inflation device including a syringe and a pressure indicator, wherein a closed inflation system is formed between the syringe and the balloon and the pressure indicator is in a non-alert state with the balloon in the deflated state;

operating the syringe to increase a pressure of the inflation system and causing the balloon to expand from the deflated state; and continuing to increase the pressure of the inflation system until the pressure indicator transitions from the non-alert state to an alert state.

* * * * *